United States Patent
Hattori et al.

(10) Patent No.: US 10,883,967 B2
(45) Date of Patent: Jan. 5, 2021

(54) GAS DETECTION ELEMENT AND DETECTION DEVICE

(71) Applicant: TAIYO YUDEN CO., LTD., Tokyo (JP)

(72) Inventors: Masashi Hattori, Takasaki (JP); Junji Oshita, Takasaki (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 202 days.

(21) Appl. No.: 15/922,678

(22) Filed: Mar. 15, 2018

(65) Prior Publication Data

US 2018/0266995 A1 Sep. 20, 2018

(30) Foreign Application Priority Data

Mar. 17, 2017 (JP) ................. 2017-052162

(51) Int. Cl.
| | |
|---|---|
| *G01N 29/02* | (2006.01) |
| *G01N 33/00* | (2006.01) |
| *G01N 5/02* | (2006.01) |
| *G01N 29/036* | (2006.01) |

(52) U.S. Cl.
CPC .......... *G01N 29/022* (2013.01); *G01N 5/025* (2013.01); *G01N 29/036* (2013.01); *G01N 33/0027* (2013.01); *G01N 2291/014* (2013.01); *G01N 2291/0255* (2013.01); *G01N 2291/0256* (2013.01); *G01N 2291/02845* (2013.01); *G01N 2291/0426* (2013.01)

(58) Field of Classification Search
CPC ..... G01N 2291/014; G01N 2291/0255; G01N 2291/0256; G01N 2291/02845; G01N 2291/0426; G01N 29/022; G01N 29/036; G01N 33/0027; G01N 5/025
USPC .............................................. 73/24.01, 24.06
See application file for complete search history.

(56) References Cited

U.S. PATENT DOCUMENTS

| | | | | |
|---|---|---|---|---|
| 4,399,686 | A | * | 8/1983 | Kindlund ............. G01N 29/036 422/98 |
| 6,612,190 | B2 | * | 9/2003 | Takeuchi .................. B06B 1/06 73/865 |
| 2004/0194534 | A1 | * | 10/2004 | Porter .................. G01N 29/022 73/24.01 |
| 2018/0266977 | A1 | * | 9/2018 | Hashizume .......... G01N 27/126 |

FOREIGN PATENT DOCUMENTS

JP         3094415 U         6/2003

* cited by examiner

*Primary Examiner* — Nimeshkumar D Patel
*Assistant Examiner* — Nashmiya S Fayyaz
(74) *Attorney, Agent, or Firm* — Law Office of Katsuhiro Arai

(57) ABSTRACT

A gas detection element includes a crystal oscillator and a gas adsorption film formed on the crystal oscillator. The gas adsorption film has a thickness that causes the detection element to have a crystal impedance of no more than 10 times the crystal impedance of the crystal oscillator on which the gas adsorption film is not formed. A resonance frequency variation of the gas detection element due to humidity variation can be kept within a certain range.

5 Claims, 2 Drawing Sheets

GAS DETECTION ELEMENT AND DETECTION DEVICE

BACKGROUND

Field of the Invention

The present invention relates to a detection element that detects a gas, as well as a detection device using such detection element.

Description of the Related Art

A QCM (quartz crystal microbalance) sensor, which is a detection element, is constituted by a crystal oscillator on which an adsorption film that selectively adsorbs a specific gas has been disposed, and it is applied as a sensor for detecting the specific gas. When the specific gas is adsorbed onto the adsorption film, such sensor measures a variation in its resonance frequency resulting from a change in mass caused by the adsorbed substance and thereby calculates the concentration of the target gas to be detected; however, the resonance frequency varies not only due to adsorption of the target gas to be detected, but also due to temperature and humidity.

Meanwhile, an AT-cut crystal oscillator exhibiting excellent temperature stability as demonstrated by the extremely small variation its temperature coefficient undergoes at or around room temperature, is used as a crystal oscillator for a gas detection element in order to reduce the error in the measured value due to temperature variation. On the other hand, precisely controlling the resonance frequency variation due to humidity variation is very difficult. Accordingly, a general practice is to measure the temperature and humidity using a temperature and humidity detection element and use the measured results to correct the value of resonance frequency variation detected by the QCM sensor (refer to Patent Literature 1, for example).

BACKGROUND ART LITERATURES

[Patent Literature 1] Japanese Utility Model Registration No. 3094415

SUMMARY

In light of the aforementioned situation, an object of the present invention is to provide a detection element whose resonance frequency variation due to humidity variation is kept within a certain range, as well as a detection device using such detection element.

Any discussion of problems and solutions involved in the related art has been included in this disclosure solely for the purposes of providing a context for the present invention, and should not be taken as an admission that any or all of the discussion were known at the time the invention was made.

To achieve the aforementioned object, the detection element pertaining to an embodiment of the present invention comprises a crystal oscillator and an adsorption film formed on the crystal oscillator.

The adsorption film has a thickness that causes the detection element to have a crystal impedance of no more than 10 times the crystal impedance of the crystal oscillator on which the adsorption film is not formed. The crystal impedance is an equivalent series resistance at a given resonance frequency when no load capacitance is applied and can be measured by any known or suitable methods/devices, e.g., using an E5100A network analyzer (Agilent Technologies, Germany) or any equivalents thereto.

According to such constitution of the present invention, a detection element which has sharp resonance characteristics and whose resonance frequency variation due to humidity variation is kept within a certain range, can be obtained.

The adsorption film may have the substantially largest thickness within the range of film thicknesses that cause the detection element to have a crystal impedance of no more than 10 times the crystal impedance of the crystal oscillator on which the adsorption film is not formed. The term "substantially" refers to 80% to 100% of the largest thickness in some embodiments.

According to such constitution, a detection element whose resonance frequency variation due to humidity variation is kept within a certain range and which demonstrates high gas adsorption power, can be obtained.

To achieve the aforementioned object, the detection device pertaining to an embodiment of the present invention comprises multiple gas detection elements.

The gas detection elements each have a crystal oscillator and an adsorption film which is provided on the crystal oscillator and which adsorbs a specific gas, wherein the adsorption film has a thickness that causes the detection element to have a crystal impedance of no more than 10 times the crystal impedance of the crystal oscillator on which the adsorption film is not formed.

According to such constitution of the present invention, a detection device whose resonance frequency variation due to humidity variation is kept within a certain range and which demonstrates high detection sensitivity, can be obtained.

The detection device may further have a humidity detection element, and a correction computing unit that corrects the detection results from the gas detection elements based on the detection result from the humidity detection element.

According to such constitution, a detection device that allows for easy correction of any resonance frequency variation due to humidity variation, can be obtained.

As described above, according to the present invention a detection element whose resonance frequency variation due to humidity variation is kept within a certain range, as well as a detection device using such detection element, can be obtained.

For purposes of summarizing aspects of the invention and the advantages achieved over the related art, certain objects and advantages of the invention are described in this disclosure. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description which follows.

BRIEF DESCRIPTION OF THE DRAWINGS

These and other features of this invention will now be described with reference to the drawings of preferred embodiments which are intended to illustrate and not to limit the invention. The drawings are greatly simplified for illustrative purposes and are not necessarily to scale.

DESCRIPTION OF THE SYMBOLS

Figure 1:
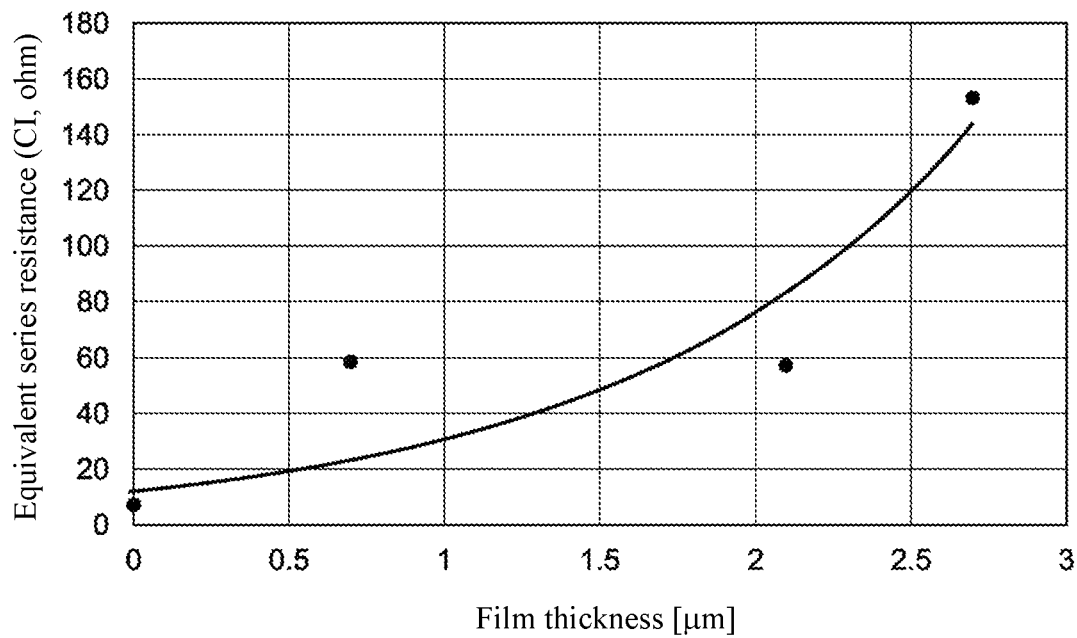
FIG. 1 is a diagram showing the relationship between the thickness of the adsorption film, and the equivalent series resistance (CI), of a gas detection element pertaining to an embodiment of the present invention.

12 First adsorption film
13 First crystal oscillator
22 Second adsorption film
23 Second crystal oscillator
32 Third adsorption film
33 Third crystal oscillator
100 Detection device
101 First gas detection element (first QCM)
102 Second gas detection element (second QCM)
103 Third gas detection element (third QCM)
122 Correction computing unit
130 Temperature and humidity sensor (sensor including a humidity detection element)

DETAILED DESCRIPTION OF EMBODIMENTS

[Detection Element]

A gas detection element pertaining to an embodiment of the present invention is explained below by referring to the drawings and table. The gas detection element has a crystal oscillator and an adsorption film which is formed on the crystal oscillator and which selectively adsorbs a specific gas. When the specific gas is adsorbed onto the adsorption film, the gas detection element measures a variation in its resonance frequency resulting from a change in mass caused by the adsorbed substance and thereby identifies whether the substance is the target gas to be detected and calculates the concentration of the target gas to be detected.

The detection element pertaining to this embodiment is constituted with the thickness of its adsorption film controlled in such a way as to achieve a crystal impedance of no more than 10 times the crystal impedance the crystal oscillator has before the adsorption film is formed. This way, a detection element whose resonance frequency variation due to humidity variation is kept within a certain range, can be obtained.

For the crystal oscillator constituting a part of the gas detection element, a crystal oscillator whose resonance frequency is 9 MHz may be used. This crystal oscillator is a crystal plate whose resonance frequency varies linearly as the temperature varies, and in this embodiment, a crystal plate whose cut angle is offset from the AT cut angle is used. The crystal oscillator in this embodiment has a circular shape of 8.6 mm in diameter and a thickness of 0.185 mm, for example. The detailed structure of the gas detection element is explained as part of the detection device mentioned below.

This embodiment explains an example of a gas detection element that uses, as its adsorption film, a copolymer of vinylidene fluoride resin (polyvinylidene fluoride) and trifluoroethylene having a property to selectively adsorb acetone, which is the target gas to be detected.

Table 1 is a table showing the adsorption film characteristics of Samples A to E that are gas detection elements whose adsorption film is made of the same material but has a different thickness. Sample A is a crystal oscillator whose adsorption film has a thickness of 0 μm, meaning that it is a crystal oscillator having no adsorption film formed on it. Samples C and D are gas detection elements according to this embodiment, or specifically gas detection elements whose adsorption film has a thickness of 2.1 μm and a thickness of 0.7 μm, respectively. Samples B and E are gas detection elements pertaining to comparative examples, or specifically gas detection elements whose adsorption film has a thickness of 2.7 μm and a thickness of 3 μm or more, respectively.

TABLE 1

| No. | Film thickness [μm] | Fr [MHz] | CI [Ω] | C0 [pF] | L1 [mH] | C1 [fF] | γ | Q |
|---|---|---|---|---|---|---|---|---|
| A | 0.0 | 8.995585 | 6.7 | 4.7 | 11.10 | 28.20 | 165 | 94297 |
| B | 2.1 | 8.934844 | 152.6 | 5.3 | 12.60 | 25.19 | 209 | 4635 |
| C | 2.1 | 8.947885 | 57.0 | 5.3 | 11.94 | 26.51 | 199 | 11776 |
| D | 0.7 | 8.978963 | 58.4 | 5.2 | 12.18 | 25.80 | 202 | 11754 |
| E | 3 or more | — | — | 4.6 | 18.20 | 16.53 | 275 | — |

FIG. 1 is a diagram showing the relationship between the thickness of the adsorption film, and the equivalent series resistance (CI), of the gas detection element.

Figure 2:
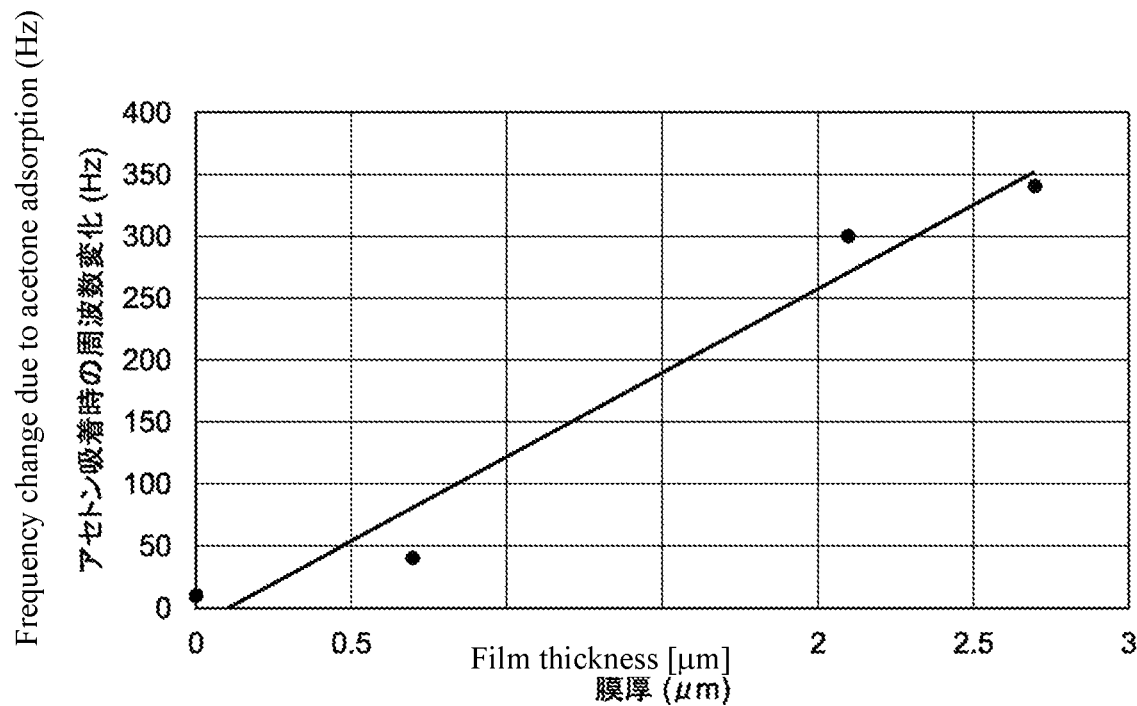
FIG. 2 is a diagram showing the relationship between the thickness of the adsorption film, and the frequency variation due to acetone adsorption, of the aforementioned gas detection element.

FIG. 2 is a diagram showing the relationship between the thickness of the adsorption film, and the frequency variation due to acetone adsorption, of the gas detection element.

Figure 3:
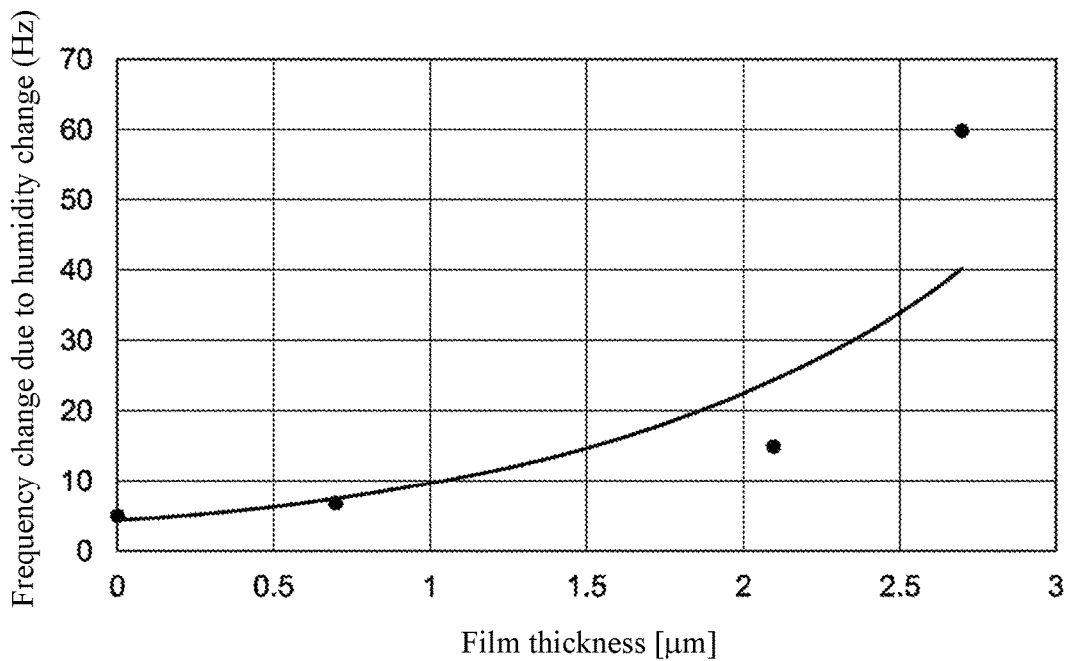
FIG. 3 is a diagram showing the relationship between the thickness of the adsorption film, and the difference in frequency variation due to humidity variation, of the aforementioned gas detection element.

FIG. 3 is a diagram showing the relationship between the difference in resonance frequency variation caused by the variation in environmental conditions from 25° C. in temperature and 40% RH in humidity to 25° C. in temperature and 50% RH in humidity, and the thickness of the adsorption film, of the gas detection element.

In Table 1, Fr represents the resonance frequency, CI represents the crystal impedance (equivalent series resistance), C0 represents the equivalent parallel capacitance, L1 represents the equivalent series inductance, and γ represents the capacitance ratio (C0/C1). Q represents the Q factor (quality factor), which is an indicator of the sharpness of resonance characteristics. The greater the value of Q, the sharper the resonance characteristics and better the gas detection sensitivity. As shown in Table 1, the resonance frequency (Fr) of the crystal oscillator (Sample A) before formation of adsorption film is approx. 9 MHz, while the CI value of Sample A is 6.7Ω. CI measurement was performed using an E5100A network analyzer manufactured by Agilent Technologies, with the drive level set to 50 μW.

The CI value is an indicator of oscillation propensity, wherein, the smaller the value, the greater the oscillation propensity. As shown in Table 1 and FIG. 1, the CI value rises, meaning that the oscillation propensity decreases, as the thickness of the adsorption film increases. The CI value remains relatively stable until the film thickness exceeds 2.1 µm, but once the film thickness exceeds 2.1 µm, the CI value rises rapidly. Also, it is evident from Table 1 that, when the film thickness exceeds 3 µm, the Q factor drops and the resonance characteristics become duller. In other words, the smaller the film thickness, the sharper the resonance characteristics. As shown in Table 1, while the CI value of Sample A is 6.7Ω, the CI value of Sample C according to this embodiment is 57.0Ω and that of Sample D, also according to this embodiment, is 58.4Ω.

Additionally, as shown in FIG. 2, there is a tendency that the gas adsorption capability increases as the thickness of the adsorption film increases, and in the example of this embodiment where the target gas to be detected is acetone gas, the frequency variation due to acetone adsorption is roughly proportional to the film thickness.

It is evident from FIG. 3 that, when the humidity rises by 10% and the film thickness exceeds 2.1 µm or so, the difference in resonance frequency variation due to humidity variation increases suddenly and the impact of humidity variation on the variation in the resonance frequency of the gas detection element becomes considerable. And, when the film thickness is in a range of 2.1 µm or less, the difference in resonance frequency variation due to humidity variation becomes roughly proportional to the film thickness, and any resonance frequency variation due to humidity variation is kept within a certain range.

This film thickness range where the difference in resonance frequency variation due to humidity variation does not increase suddenly, or 2.1 µm or less in this embodiment, can be achieved by controlling the thickness of the adsorption film so that the crystal impedance of the gas detection element becomes no more than 10 times the crystal impedance of the crystal oscillator on which no adsorption film is formed.

In this embodiment, the CI value of Sample A is 6.7Ω, and Samples C and D whose CI value is within the range of no more than 10 times this value, or 67Ω or less, provide gas detection elements which have sharp resonance characteristics and whose resonance frequency variation due to humidity variation is kept within a certain range.

Based on the above, a gas detection element which has sharp resonance characteristics and whose resonance frequency variation due to humidity variation is kept within a certain range can be obtained by providing an adsorption film whose thickness is such that the crystal impedance of the gas detection element becomes no more than 10 times the crystal impedance of the crystal oscillator on which no adsorption film is formed.

More preferably the crystal impedance of the gas detection element is at least 1.1 times the crystal impedance of the crystal oscillator on which no adsorption film is formed; when the crystal impedance is less than 1.1 times, the thickness of the adsorption film becomes too small and the effectiveness of gas adsorption becomes smaller.

And, a detection device equipped with such gas detection element allows for easy correction of the resonance frequency variation due to humidity variation, because the resonance frequency variation due to humidity variation is kept within a certain range and the resonance frequency variation due to humidity variation is roughly proportional to the film thickness.

In the case of a gas detection element having an adsorption film whose thickness is such that the crystal impedance of the gas detection element becomes greater than 10 times the crystal impedance of the crystal oscillator on which no adsorption film is formed, the resonance frequency variation due to humidity variation increases suddenly. This is why correcting the resonance frequency variation due to humidity variation becomes complicated in the case of a detection device equipped with such gas detection element, because the resonance frequency variation due to humidity variation is not proportional to the film thickness.

In addition, the gas adsorption capability of the adsorption film increases as the thickness of the adsorption film increases, as shown in FIG. 2. This means that, by setting an adsorption film thickness that corresponds to the largest film thickness within the range of adsorption film thicknesses that cause the gas detection element to have a crystal impedance of no more than 10 times the crystal impedance of the crystal oscillator on which no adsorption film is formed, a gas detection element can be obtained which is subject to no more than a certain level of impact from humidity, which exhibits high gas adsorption capability, and which offers good detection sensitivity. It should be noted that the lower-limit value of adsorption film thickness is not limited in any way. Although the specific values differ depending on the material used for the adsorption film, generally a gas detection element can function as such if its adsorption film has a thickness of at least 0.01 µm.

It should be noted that, while in the example of this embodiment the material of the adsorption film is a copolymer of vinylidene fluoride resin (polyvinylidene fluoride) and trifluoroethylene, the same effects can be achieved with other materials. For example, the present invention can also be applied to materials such as cellulose acetate butyrate.

Traditionally an adsorption film is formed to an optimal thickness that differs for each material used for the adsorption film, based on the adsorption characteristics and resonance characteristics of the material. On the other hand, under the present invention, regardless of the type of materials, an adsorption film is formed to the largest film thickness within the range of film thicknesses that cause the gas detection element to have a crystal impedance of no more than 10 times the crystal impedance of the crystal oscillator before formation of adsorption film (Sample A).

For the method for forming an adsorption film, any known method may be used; for example, the casting method, spin coat method, sputter deposition, etc., may be used. In this embodiment, multiple gas detection elements each are manufactured by forming an adsorption film on a crystal oscillator to a different thickness according to a known or any other suitable method, after which the crystal impedance of each manufactured gas detection element is measured and an adsorption film thickness is determined which is the largest film thickness among those of the multiple gas detection elements within the range of film thicknesses that achieve a crystal impedance of no more than 10 times that of the crystal oscillator before formation of adsorption film, and accordingly, a gas detection element having this adsorption film thickness is manufactured.

[Detection Device]

Next, a detection device using the aforementioned gas detection element whose adsorption film thickness has been controlled to the largest film thickness within the range of film thicknesses that achieve a crystal impedance of no more than 10 times that of the crystal oscillator before formation of adsorption film, is explained.

Figure 4:
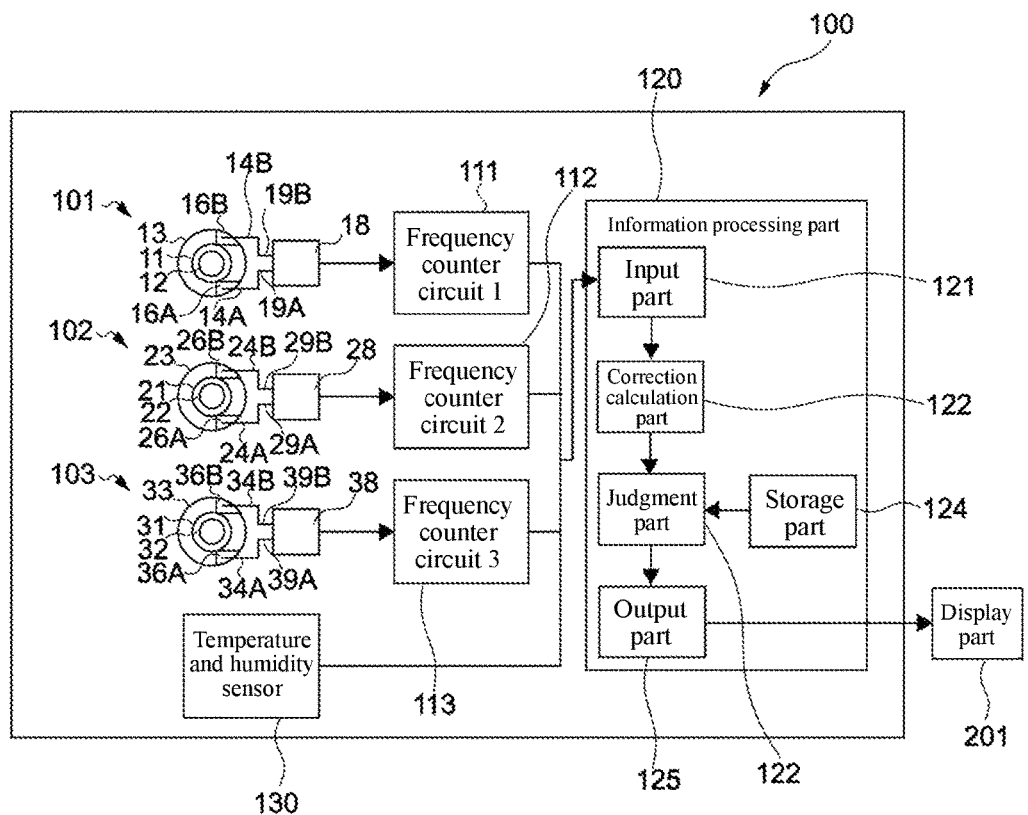
FIG. 4 is a diagram showing the constitution of a detection system equipped with a detection device in which the aforementioned gas detection element is used.

A detection device equipped with multiple detection elements, each having an adsorption film that has been formed by controlling its thickness based on the crystal impedance as described above, is explained below by referring to the drawings. FIG. 4 shows the constitution of a detection system equipped with the detection device.

The detection system comprises a detection device 100 and a display device having a display part 201 that displays the result of detection by the detection device 100.

The detection device 100 comprises: a board (not illustrated); a first QCM sensor element (hereinafter referred to as "first QCM") 101 as a first gas detection element; a second QCM sensor element (hereinafter referred to as "second QCM") 102 as a second gas detection element; a third QCM sensor element (hereinafter referred to as "third QCM") 103 as a third gas detection element; a first frequency counter circuit 111; a second frequency counter circuit 112; a third frequency counter circuit 113; an information processing part 120; and a temperature and humidity sensor 130. The temperature and humidity sensor 130 comprises both a temperature detection element and a humidity detection element.

The three QCMs 101 to 103 are each constituted by a crystal oscillator as an oscillator, and an adsorption film which is provided on the crystal oscillator and which adsorbs a specific gas, and they all have the same basic structure except that the type of adsorption film is different. Since the resonance frequency of the crystal oscillator decreases proportionally to the weight of the gas adsorbed onto the adsorption film, it is possible to measure the variation in the resonance frequency of each crystal oscillator and determine whether or not the detected gas contains acetone, toluene or formaldehyde, for example, and also calculate the concentration of each target gas to be detected. It should be noted that the target gas to be detected can be changed as desired by changing the type of adsorption film.

In this embodiment, a crystal oscillator whose resonance frequency is 9 MHz may be used for the detection element. The crystal oscillator that constitutes a part of the detection element is a crystal plate whose resonance frequency varies linearly as the temperature varies, and in this embodiment, a crystal plate whose cut angle is offset from the AT cut angle is used. The crystal oscillator has a circular shape of 8.6 mm in diameter, with a thickness of 0.185 mm and a resonance frequency of 9 MHz.

The first QCM 101 (second QCM 102, third QCM 103) has: a first crystal oscillator 13 (second crystal oscillator 23, third crystal oscillator 33); an electrode 11 (21, 31); a first adsorption film 12 (second adsorption film 22, third adsorption film 32); a lead land 16A (26A, 36A); a lead land 16B (26B, 36B); a lead 14A (24A, 34A); a lead 14B (24B, 34B); a pin terminal 19A (29A, 39A); and a pin terminal 19B (29B, 39B).

The electrode 11 (21, 31) is formed on both faces of the crystal oscillator 13 (23, 33), and the adsorption film 12 (22, 32) is formed on the electrode 11 (21, 31) that has been formed on one face of the crystal oscillator 13 (23, 33). The lead land 16A (26A, 36A) is integrally formed with the electrode 11 (21, 31) formed on one face of the crystal oscillator, while the other lead land 16B (26B, 36B) is integrally formed with the electrode 11 (21, 31) formed on the other face of the crystal oscillator.

The leads 14A (24A, 34A) and 14B (24B, 34B) are each constituted by a metal spring material, and placed in parallel with each other.

The lead 14A (24A, 34A) is such that one end is electrically connected to the electrode 11 (21, 31) formed on one face of the crystal oscillator via the lead land 16A (26A, 36A), and the other end is connected to the pin terminal 19A (29A, 39A). The lead 14B (24B, 34B) is such that one end is electrically connected to the electrode 11 (21, 31) formed on the other face via the lead land 16B (26B, 36B), and the other end is connected to the pin terminal 19B (29B, 39B).

The pin terminals 19A (29A, 39A) and 19B (29B, 39B) are each supported on a terminal block 18 (28, 38) provided on the board, and the crystal oscillator 13 (23, 33) is supported on the terminal block 18 (28, 38) in a freely vibrable manner.

The pin terminals 19A (29A, 39A) and 19B (29B, 39B) of the QCM 101 (102, 103) are each connected to an oscillation circuitry which is not illustrated, and driving voltage is applied to the QCM 101 (102, 103) accordingly. When driving voltage is applied to the QCM 101 (102, 103), the crystal oscillator 13 (23, 33) vibrates at its natural resonance frequency (9 MHz in this example).

And, when the adsorption film 12 (22, 32) adsorbs a gas, its mass changes and the oscillation frequency of the crystal oscillator 13 (23, 33) drops according to the adsorbed amount. The first QCM 101, second QCM 102, and third QCM 103 are connected to the first frequency counter circuit 111, second frequency counter circuit 112, and third frequency counter circuit 113, respectively. The first frequency counter circuit 111 (second frequency counter circuit 112, third frequency counter circuit 113) detects the resonance frequency of the first QCM 101 (second QCM 102, third QCM 103). Each frequency counter circuit 111 to 113 outputs an electrical signal corresponding to the detected resonance frequency, to the information processing part 120.

Each adsorption film 12, 22, or 32 is constituted so that its thickness becomes the largest in the range of film thicknesses that achieve a crystal impedance of no more than 10 times that of the crystal oscillator before formation of adsorption film.

The adsorption film 12 is made of a copolymer of vinylidene fluoride resin (polyvinylidene fluoride) and trifluoroethylene, with a thickness of 1 μm. The adsorption film 22 is made of a copolymer of vinylidene fluoride resin (polyvinylidene fluoride), trifluoroethylene, and ethylene chloride trifluoride, with a thickness of 1 μm. The adsorption film 32 is made of a cellulose acetate butyrate, with a thickness of 1 μm. The adsorption film 12 has a property to adsorb acetone, the adsorption film 22 has a property to adsorb toluene, and the adsorption film 32 has a property to adsorb formaldehyde, and in this embodiment, the first QCM 101 is used to detect acetone, the second QCM 102 is used to detect toluene, and the third QCM 103 is used to detect formaldehyde.

The temperature and humidity sensor 130 detects the temperature and humidity of the ambience where the detection device 100 is placed.

In this embodiment, the resonance frequencies detected respectively by the QCMs 101 to 103 are corrected, based on the temperature detected by the temperature and humidity sensor 130, in a manner cancelling the variations in their resonance frequencies caused by temperature. Data of resonance frequency variations corresponding to temperature is stored, for each adsorption film, in the below-mentioned storage part 124 of the information processing part 120 beforehand.

Also, the resonance frequencies detected respectively by the QCMs 101 to 103 are corrected, based on the humidity detected by the temperature and humidity sensor 130, by the below-mentioned correction computing unit 122 of the information processing part 120, in a manner correcting for the variations in their resonance frequencies caused by humidity. Data of resonance frequency variations corresponding to humidity is stored, for each adsorption film, in the below-mentioned storage part 124 of the information processing part 120 beforehand.

The information processing part 120 has an input part 121, a correction computing unit 122, a judgment part 123, a storage part 124, and an output part 125.

Input to the input part 120 are an electrical signal corresponding to the resonance frequency of the first QCM 101 detected by the first frequency counter circuit 111, an electrical signal corresponding to the resonance frequency of the second QCM 102 detected by the second frequency counter circuit 112, an electrical signal corresponding to the resonance frequency of the third QCM 103 detected by the third frequency counter circuit 113, and the temperature and humidity information detected by the temperature and humidity sensor 130.

The correction computing unit 122 corrects the variation in the resonance frequency of each QCM 101 to 103 based on what has been input to the input part 120; namely, the electrical signal corresponding to the resonance frequency being the result of detection by each QCM 101 to 103, and the temperature and humidity information being the result of detection by the temperature and humidity sensor 130, and the information relating to resonance frequency variation due to temperature variation and humidity variation as input from the storage part 124.

Here, the adsorption films 12, 22, 23 all have a film thickness controlled to achieve a crystal impedance of no more than 10 times that of the crystal oscillator before formation of adsorption film, which means that the adsorption films 12, 22, 32 have been controlled to have a film thickness in a range where the difference in frequency variation due to humidity variation is roughly proportional to the thickness of the adsorption film, and consequently the resonance frequency variation due to humidity variation is kept within a certain range. This makes the correction performed by the correction computing unit 122, which is to correct for the variation in the resonance frequency of the gas detection element caused by humidity variation, easy.

The judgment part 123 identifies whether or not the detected gas is the target gas, and calculates the concentration of the target gas to be detected, based on the variation in the resonance frequency of each QCM 101 to 103 as corrected by the correction computing unit 122.

The output part 125 outputs the judgment result from the judgment part 123 to the display device. The judgment result is displayed on the display part 201 of the display device.

As described above, the detection device 100 in this embodiment keeps the impact of humidity within a certain range and allows for easy correction of the variation in the resonance frequency of the gas detection element caused by humidity variation. As a result, a detection device offering high detection accuracy can be obtained.

In the present disclosure where conditions and/or structures are not specified, a skilled artisan in the art can readily provide such conditions and/or structures, in view of the present disclosure, as a matter of routine experimentation. Also, in the present disclosure including the examples described above, any ranges applied in some embodiments may include or exclude the lower and/or upper endpoints, and any values of variables indicated may refer to precise values or approximate values and include equivalents, and may refer to average, median, representative, majority, etc. in some embodiments. Further, in this disclosure, "a" may refer to a species or a genus including multiple species, and "the invention" or "the present invention" may refer to at least one of the embodiments or aspects explicitly, necessarily, or inherently disclosed herein. The terms "constituted by" and "having" refer independently to "typically or broadly comprising", "comprising", "consisting essentially of", or "consisting of" in some embodiments. In this disclosure, any defined meanings do not necessarily exclude ordinary and customary meanings in some embodiments.

The present application claims priority to Japanese Patent Application No. 2017-052162, filed Mar. 17, 2017, the disclosure of which is incorporated herein by reference in its entirety including any and all particular combinations of the features disclosed therein.

It will be understood by those of skill in the art that numerous and various modifications can be made without departing from the spirit of the present invention. Therefore, it should be clearly understood that the forms of the present invention are illustrative only and are not intended to limit the scope of the present invention.

We claim:
1. A gas detection element comprising:
a crystal oscillator having an initial crystal impedance; and
a gas adsorption film formed on the crystal oscillator wherein the gas adsorption film has a thickness that causes the gas detection element to have a crystal impedance of no more than 10 times the initial crystal impedance.
2. The gas detection element according to claim 1, wherein the gas adsorption film has a substantially largest thickness in a range of film thicknesses that cause the detection element to have a crystal impedance of no more than 10 times the initial crystal impedance.
3. The gas detection element according to claim 1, wherein the gas adsorption film has a thickness that cause the detection element to have a crystal impedance of at least 1.1 times the initial crystal impedance.
4. A gas detection device comprising:
multiple gas detection elements, each having a crystal oscillator having an initial crystal impedance and a gas adsorption film which is provided on the crystal oscillator and which adsorbs a specific gas,
wherein the gas adsorption film of said each gas detection element has a thickness that causes said each gas detection element to have a crystal impedance of no more than 10 times the initial crystal impedance.
5. The gas detection device according to claim 4, further comprising:
a humidity detection element and a correction computing unit that corrects a detection result from said each gas detection element based on a detection result from the humidity detection element.

* * * * *